US008431064B2

(12) United States Patent
Greiner et al.

(10) Patent No.: US 8,431,064 B2
(45) Date of Patent: Apr. 30, 2013

(54) METHOD OF USING NANOSCALED POLYMER FIBERS AS CARRIERS FOR AGRICULTURAL SUBSTANCES

(75) Inventors: Andreas Greiner, Amoneburg (DE); Hans E. Hummel, Giessen (DE); Joachim H. Wendorff, Nauheim (DE); Mathias Becker, Saarbrucken (DE); Roland Dersch, Marburg (DE)

(73) Assignees: Phillips-Universitat Marburg, Marburg (DE); Justus-Liebig Universitat Giessen, Giessen (DE)

(*) Notice: Subject to any disclaimer, the term of this patent is extended or adjusted under 35 U.S.C. 154(b) by 0 days.

(21) Appl. No.: 13/204,778

(22) Filed: Aug. 8, 2011

(65) Prior Publication Data

US 2011/0300383 A1 Dec. 8, 2011

Related U.S. Application Data

(62) Division of application No. 11/597,516, filed as application No. PCT/DE2005/000984 on May 30, 2005, now Pat. No. 8,017,061.

(30) Foreign Application Priority Data

May 28, 2004 (DE) ......................... 10 2004 026 745

(51) Int. Cl.
*D06M 10/00* (2006.01)
*H05B 7/00* (2006.01)

(52) U.S. Cl.
USPC .......................................................... 264/465

(58) Field of Classification Search .................. 264/129, 264/211, 465; 47/58.1; 111/118, 130, 200
See application file for complete search history.

(56) References Cited

U.S. PATENT DOCUMENTS

| | | | | |
|---|---|---|---|---|
| 4,845,888 | A | 7/1989 | Lahalih et al. | |
| 5,024,789 | A | 6/1991 | Berry | |
| 2002/0096246 | A1 | 7/2002 | Sennet et al. | |
| 2003/0108743 | A1 | 6/2003 | Anderson | |
| 2003/0215624 | A1 | 11/2003 | Layman et al. | |
| 2004/0076681 | A1* | 4/2004 | Dennis et al. | 424/489 |
| 2005/0281957 | A1 | 12/2005 | Cooper et al. | |
| 2007/0035055 | A1* | 2/2007 | Gee et al. | 264/465 X |

FOREIGN PATENT DOCUMENTS

| | | | |
|---|---|---|---|
| DE | 703750 | | 3/1941 |
| DE | 40 35 223 | | 5/1991 |
| DE | 42 06 856 | A1 | 9/1993 |
| DE | 42 06 856 | C2 | 9/1993 |
| DE | 43 39 443 | | 5/1995 |
| DE | 44 13 739 | A1 | 10/1995 |
| DE | 44 13 739 | C2 | 10/1995 |
| DE | 195 45 919 | | 6/1996 |
| DE | 195 29 409 | | 2/1997 |
| DE | 196 40 268 | | 4/1998 |
| DE | 196 45 842 | | 5/1998 |
| DE | 198 34 025 | | 2/2000 |
| DE | 100 23 456 | | 2/2001 |
| DE | 199 61 330 | | 6/2001 |
| DE | 100 40 897 | A1 | 3/2002 |
| DE | 100 40 897 | B4 | 3/2002 |
| DE | 100 41 148 | | 3/2002 |
| DE | 101 16 751 | A1 | 10/2002 |
| DE | 101 16 751 | C2 | 10/2002 |
| DE | 101 22 753 | | 11/2002 |
| DE | 101 15 225 | | 12/2002 |
| DE | 101 28 531 | | 12/2002 |
| DE | 101 55 385 | | 5/2003 |
| DE | 102 17 697 | | 11/2003 |
| DE | 696 27 281 | | 11/2003 |
| EP | 0 005 035 | A1 | 10/1979 |
| EP | 0 005 035 | B1 | 9/1981 |
| EP | 0 095 940 | A2 | 12/1983 |
| EP | 0 095 940 | A3 | 5/1985 |
| EP | 0 095 940 | B1 | 5/1988 |
| EP | 0 799 928 | A3 | 7/1988 |
| EP | 0 799 928 | A2 | 10/1997 |
| EP | 0 799 928 | B1 | 12/2004 |
| JP | 01266210 | | 10/1989 |
| JP | 05311509 | | 11/1993 |
| JP | 07268772 | | 10/1995 |
| JP | 08120524 | | 5/1996 |
| JP | 2003-328229 | | 11/2003 |
| WO | 91/01086 | | 2/1991 |
| WO | 91/01695 | | 2/1991 |
| WO | 98/03267 | | 1/1998 |
| WO | 99/31963 | | 7/1999 |
| WO | 01/09414 | | 2/2001 |
| WO | 01/26610 | | 4/2001 |

(Continued)

OTHER PUBLICATIONS

P. Baumgarten, "Electrostatic Spinning of Acrylic Microfibers", *Journal of Colloid and Interface Science*, vol. 36, No. 1, May 1971, pp. 71-79.

(Continued)

*Primary Examiner* — Leo B Tentoni
(74) *Attorney, Agent, or Firm* — Clark & Brody

(57) ABSTRACT

The invention relates to supports consisting of nanoscalar polymer fibers, polymer tubes or hollow fibers for the application and targeted and/or delayed release of ingredients, in particular, agricultural active ingredients. The invention also relates to a method and a device for the production of supports of this type in a charged or empty state. The method and device use electrospinning technology.

4 Claims, No Drawings

FOREIGN PATENT DOCUMENTS

| WO | 01/27365 | 4/2001 |
|---|---|---|
| WO | 02/16680 | 2/2002 |
| WO | 02/092339 | 11/2002 |
| WO | 03/034822 | 5/2003 |

OTHER PUBLICATIONS

M. Bognitzki et al., "Polymer, Metal, and Hybrid Nano- and Mesotubes by Coating Degradable Polymer Template Fibers (TUFT Process)", *Adv. Mater.* 2000, 12, No. 9, pp. 637-640.

M. Bognitzki et al., "Nanostructured Fibers via Electrospinning", *Adv. Mater.* 2001, 13, No. 1, Jan. 5, pp. 70-72.

M. Bognitzki et al., "Preparation of Fibers With Nanoscaled Morphologies: Electrospinning of Polymer Blends", *Polymer Engineering and Science*, Jun. 2001, vol. 41, No. 6, pp. 982-989.

T.W. Brooks et al., "Experience With the First Commercial Pheromone Communication Disruptive for Suppression of an Agricultural Insect Pest", Chemical Ecology: Odour Communication in Animals, c 1979 Elsevier/North-Holland Biomedical Press, pp. 375-388.

T.W. Brooks et al., "Experience in Using a Hollow Fiber Controlled Release Formulation in Pheromone Mediated Suppression of Pectinophora Gossypiella Under Humid Tropical Conditions", Controlled Release of Bioactive Materials, c 1980 Academic Press, Inc., pp. 227-236.

N. Cardarelli, "The Efficacy, Environmental Impact and Mechanism of Release and Dispersal of Pesticidal Materials Emitted from a Controlled-Release Dispenser", *Pesticidal Materials*, (1979) pp. 744-753.

Z. Chen et al., "Structure of Poly(ferrocenyldimethylsilane) in Electrospun Nanofibers", *Macromolecules* 2001, 34, 6156-6158.

J.M. Deitzel et al., "Controlled deposition of electrospun poly(ethylene oxide) fibers", *Polymer* 42 (2001) 8163-8170.

H. Fong et al., "Elastomeric Nanofibers of Styrene-Butadiene-Styrene Triblock Copolymer", *Journal of Polymer Science: Part B: Polymer Physics*, vol. 37, (1999) 3488-3493.

H.B. Hopfenberg et al., "The Diffusion and Sorption of Gases and Vapours in Glassy Polymers", *The Physics of Glass Polymers*, (1973) Chapter 9, pp. 504-547.

H. Hummel et al., "Orientation disruption in *Diabrotica virgifera virgifera* by the plant kairomone p-methoxy-cinnamaldehyde (MCA) and other semiochemicals", 2nd FAO WCR/TCP Meeting and 4th Intl. IWGO Workshop, Oct. 28-30, 1997, Godollo, Hungary, pp. 36-37.

H. Hummel et al., "*Diabrotica Barberi* and *D. virgifera virgifera* Fail to Orient Towards Sticky Traps in Maize Fields Permeated With the Plant Kairomones 4-Methoxy-Phenylethanol and 4-Methoxy-Trans-Cinnamaldehyde", *Med. Fac. Landbouww. Univ. Gent.* 61/3b, 1996 pp. 1011-1017.

H. Hummel et al., "Orientation Disruption of Western Corn Rootworm Beetles by Air Permeation with Host Plant Kairomone Mimics", IWGO Newsletter, 1998, (18)1, p. 34.

R. Jaeger et al., "Chain Packing in Electro-Spun Poly(ethylene oxide) Visualized by Atomic Force Microscopy", *Macromolecules* 1996, 29, 7634-7636.

L. Larrondo et al., "Electrostatic Fiber Spinning from Polymer Melts. I. Experimental Observations on Fiber Formation and Properties", *Journal of Polymer Science: Polymer Physics Edition*, vol. 19, 909-920 (1981).

A.F. Kydonieus et al., "Formulations and Equipment for Large Volume Pheromone Applications by Aircraft", Insect Pheromone Technology ACS Symposium #190, Washington DC (1982) pp. 176-191.

T. deV. Naylor, "Comprehensive Polymer Science", S.G. Allen Ed., Pergamon Press, NY, 1989.

J. Plimmer et al., "Insect Pheromones: Some Chemical Problems Involved in Their Use and Development", Chemical Ecology: Odour Communication in Animals, 1979, pp. 249-260.

D. Reneker et al., "Bending instability of electrically charged liquid jets of polymer solutions in electrospinning", *Journal of Applied Physics*, vol. 87, No. 9, May 1, 2000, pp. 4531-4547.

D. Reneker et al., "Nanometre diameter fibres of polymer, produced by electrospinning", *Nanotechnology* 7 (1996) 216-223.

H. Shorey et al., "Use of Puffers for Disruption of Sex Pheromone Communication of Codling Moths (Lepidoptera: Tortricidae) in Walnut Orchards", *Physiological and Chemical Ecology*, vol. 25, No. 6, Dec. 1996, pp. 1398-1400.

Z. Sun et al., "Compound Core-Shell Polymer Nanofibers by Co-Electrospinning", *Adv. Mater.* 2003, 15, No. 22, Nov. 17, pp. 1929-1932.

J. Weatherston et al., "Methodology for Determining the Release Rates of Pheromones From Hollow Fibers", E. R. Mitchell ed. (1981), Management of Insect Pests with Semiochemicals; Concept and Practice, Plenum Press, NY, pp. 425-443.

L. Wennemann et al., "*Diabrotica* Beetle Orientation Disruption with the Plant Kairomone Mimic 4-methoxy cinnamaldehyde in *Zea mays* L." Mitt. Dtsch. Ges. Allg. Agnew, Ent. 13, Giessen 2001, pp. 209-214.

L. Wennemann et al., "Analysis of a Novel Formulation of the Plant Kairomone Mimic 4-Methoxycinnamaldehyde (MCA) Using UV Spectrometry", XXI IWGO Conference, VII Diabrotica Subgroup Mtg. Proceedings, Padova, Oct. 27-Nov. 3, 2001, pp. 69-75.

L. Wennemann et al., "Use of MCA (4-Methoxycinnamaldehyde) as an Orientation Disruption Tool for Adult Western Corn Rootworm *Diabrotica virgifera virgifera* Leconte", XXI IWGO Conference, VII *Diabrotica* Subgroup Mtg., Proceedings, Padova, Oct. 27-Nov. 3, 2001, pp. 77-82.

D. Reneker et al., "Nanometre diameter fibres of polymer, produced by electrospinning", *Nanotechnology* 7, (1996) 216-223.

J. Doshi et al., "A Novel Electrospinning Process", *Polymer News*, 1995, vol. 20, pp. 206-213.

\* cited by examiner

METHOD OF USING NANOSCALED POLYMER FIBERS AS CARRIERS FOR AGRICULTURAL SUBSTANCES

This is a divisional application of application Ser. No. 11/597,516, filed on Jan. 2, 2008, now U.S. Pat. No. 8,017,061, which is a national stage application based on PCT application no. PCT/DE2005/000984, filed on May 30, 2005.

The invention at hand concerns the use of nanoscaled, in particular nanostructured, polymer fibers as carriers or/and controlled release systems for agricultural active substances, a method for the delivery of agricultural active substances, as well as a device for performing this procedure.

DESCRIPTION AND TECHNICAL STATE OF THE ART

Active substances known for the treatment of plants or/and soil, which occur naturally or are extracted by means of chemical methods or are produced by means of chemical and/or microbiological processes, are understood to be "agricultural active substances", such as, for example: fungicides, bactericides, insecticides, acaricides, nematicides, helminthicides, herbicides, molluscicides, rodenticides, algicides, aphicides, larvicides, ovicides, attractants in the form of animal nutriment, antifeedants, kairomones, repellents, game deterrents. System means are: plant growth regulators or plant nutrients, such as, e.g. but not exclusively, fertilizer.

In particular, substances which impact the animals surrounding the plants are understood as insecticides As well as chemically or microbiologically produced substances, these substances can also be naturally-occurring active substances, such as extracts, e.g. from the neem tree or the quassia root or also such substances which impact the sexual behavior of the animals surrounding the plants, such as e.g. pheromones.

It should be mentioned as an example for the commercial importance of such substances that, in particular for the prevention of the infestation of maize plants by the western corn rootworm (*Diabrotica virgifera virgifera*), several millions of euros are currently spent worldwide. In case of the infiltration of only this pest insect, which has not been detected until 2003, in Germany up to 25 millions of euros would have to be spent for the protection of the maize plants, according to estimations of the Biological Federal Agency for Agriculture and Forestry.

There is an entire array of methods known for the delivery of substances, which can be applied to the soil or plants.

These are the delivery of
1) liquids in drop form through splashing, spraying, misting, spreading as well as droplet irrigation,
2) solids in the form of granules and powders, as well as
3) gaseous substances through different types of dispensers.

Examples of 1 are the long-conventional methods for the delivery or distribution, with watering can, hand sprayer, backpack sprayer, tractor, helicopter and airplane.

Examples of 2 are, along with granules and powders, also adsorbates on solid natural or artificial particles, e.g. corncob pellets on which the kairomone MCA has been absorbed (Hummel and Metcalf, 1996; Hummel et al., 1997; Wennemann and Hummel, 2001). A lot of development work has already been spent on the technology of the dispensers. A critical overview of the state of the art achieved up to 1982 can be found in the monograph from Leonhardt and Beroza (1982). Further examples are found in Hummel and Müller (1984). The method in 2 is typically used for the delivery of fertilizer.

Examples of 3 are pheromones which are vaporized from half-open PTFE capillaries, e.g. formulated with adhesive and distributed from airplane (Brooks et al., 1979). Also to be mentioned are double-chambered dispensers of the company Hercon Laboratories Corp., York, Pa., USA for pheromones, such as those which found use by the BASF AG company in pomiculture and viniculture. Finally to be mentioned are the "Lecture-bottle" buffer systems, described by Shorey et al. (1996), in which compressed signal substance solutions are stored and from which formulations are dispensed through valves by radio command.

In the enclosed bibliography A, numerous sources are listed, in which a critical overview of the systems available until a short while ago is possible.

The disadvantage of these methods is that, in general, the application of the active substances is not continuous, extends only over a very limited space of time, and that disruptive factors such as wind and rain impact this application as well as the time which the active substances remain on the target surfaces (e.g. the soil in the area of plants to be grown or already grown or on the surfaces of plants) very negatively. This has the consequence that at a desired application of active substances over a long space of time a repeated delivery of the active substance is necessary, which is associated with raised costs. The alternative of a nonrecurring delivery of the total amount of active substance bears the risk that the active substances are displaced to non-targeted surfaces and, thus, at least a financial loss for the user, if not even undesired ecological effects presenting in non-targeted surfaces. Evacuation through water into the soil or in lakes, brooks and rivers is a typical example.

Here, carrier materials or systems, as described for medicinal active substances but also active substances for agriculture, are advantageous.

The patent specification n° 703750 describes the production of tubes, tapes, pastes from polyvinyl chloride for therapeutic applications in bandages, medical clothing.

DE 19645919 A1 describes molds containing active substances on the basis of biologically degradable thermoplastic synthetics for combating parasites, insects, which cause damage to plants, wherein the molds are available as tapes, medallions, earmarks or soil granules.

DE 19645842 A1 describes means for the treatment of plants, comprising thermoplastically-processable, biologically degradable polymers provided with at least one agrochemical active substance, whereby the application occurs through molds, such as foils.

DE 10128531 A1 describes water-soluble or water-dispersable graft polymerisates as coating material, packaging material or matrix creators for agrochemicals.

DE 10115225 A1 describes molds containing active substances on the basis of thermoplastically-processable polyurethanes for combating parasites, wherein the molds are tapes and medallions. DE 19529409A1 describes thermoplastic and biologically degradable polymers, which, amongst other things, are suitable for delayed release of active substances.

DE 198 34025 A1 describes microcapsules for the controlled release of active substance.

DE 4206856 A1 describes fibers for protection against moths.

The patent specification 01266210 A describes bacterial and fungicidal twines.

WO 99131963 describes polymer fibers for the growth of plants and as a soil substitute, as a cultivation medium, which contains means for growth.

D01F8114 describes microbacterial fibers and tissue for textiles.

EP 0799928 A1 describes fiber-shaped materials, which are antibacterially and antifungally equipped for applications in filters.

DE 101 16751 A1 describes likewise bioactive fiber products, which show antibacterial and fungicidal effects for the area of textiles. O8120524 A describes hollow polymer fibers, which contain insecticides or flavor additive in their core, wherein the release is controlled by the polymer wall.

077268772 A describes hollow fibers in the range between 7 and 150 micrometers, which contain perfumes, antibacterial or fungicidal active substances in their interior. 05311509 A describes, finally, synthetic acryl threads with insecticidal qualities and good colorability.

DE 196 40 268 (BASF) describes foil-coated fertilizers, encompassing single coated volumes of a nutrient-containing substance, wherein the foil coating the nutrient-containing substance contains a water-permeable polymer, which should preferably be biologically degradable. The method for the production of this fertilizer is very complex, since first the volumes are applied to a first foil, then a second foil is applied, and then, through individual welding or similar methods, both foils must be connected in the areas between the volumes.

Indeed, the subject matter of this DE 196 40 268 allegedly features the advantage over the matters of the aforementioned specifications, e.g. DE-OS 40 35 223, WO 91/01086, or U.S. Pat. No. 4,845,888 that the release of the active substances (fertilizer) occurs immediately after the delivery and in a targeted manner, contrarily to the release profiles of the aforementioned applications, according to which the release does not occur at the beginning, but after perforation or rotting of the carriers. However, the subject matter of DE 196 40 268 is characterized by, apart from limited choice options concerning the suitable polymer materials (permeability for water vapor not higher than 100 g/($m^2$ and day)), the disadvantage that the "adjustability" of the release, due to "transport blockades" (diffusion has been mentioned as the main transport effect), is difficult. At the stated sizes of the "volumes", i.e. the areas with fertilizers of 20 $cm^2$, the "transport pathways" from the area of higher fertilizer concentration to the wall can easily result in being very high. Thus, from this, generally smaller-structured carriers should be preferred.

None of these aforementioned substances or carriers, processes, in particular for delivery, and methods, in particular for delayed release, is in the position to apply agricultural active substances, e.g. agrochemically functional substances, such as e.g. pheromones, insecticides, fungicides, extensively or/and very targeted and with a very low application of active substance per surface, or/and with very pronounced time-delay or/and with high spatial homogeneity in agriculture, forestry or in the garden loco-regionally targeted to the soil or/and, in particular, plants, to maintain the active substances at the site under different weather conditions, to adjust to the growth of the plant and, at the end of the growth period, to decompose into biologically harmless substances or to decompose into substances which naturally occur in nature and in the concentrations encountered there.

Molds, such as those known in the technical state of the art, foils, tapes, medallions, hollow fibers, fibers in a diameter range clearly over 1 micrometer are far from accomplishing these claims. In every case, the ratio of surface to the volume of the carrier is fundamental for the adjustment of the release. This ratio is particularly advantageous in nanostructured fibers and increases very rapidly with decreasing fiber diameter.

Already, several, in principle, suitable carriers of active substances and their methods of production are known as results of "nano-research".

Electrospinning represents a particularly economical method, both for the gentle embedding of the active substances in the carrier, as well as for control of the fiber diameter down to the nanometer scale.

Details to the process of electrospinning or electro spinning are, e.g. described in D. H. Reneker, I. Chun, Nanotechn. 7, 216 (1996) or Fong, H.; Reneker, D. H.; J. Polym. Sci, Part B 37 (1999), 3488 and in DE 100 23 45 69.

In the case of electrospinning, the formation of fibers occurs by means of a high electrical tension, attached between a nozzle and a counter electrode (see Bibliography 1-10). The material to be spun is present hereby in the form of a melt or/and a solution and is transported through the nozzle. The electrical field causes a deformation of the droplet leaving the nozzle via induced charges; a fine material flow is formed, which is accelerated in the direction of the counter electrode. The material flow is deformed hereby, reticulates—as in lightening charges—and is finally deposited onto a substrate. During the spinning process, the solvent evaporates or the melt cools, respectively.

The fibers are deposited at a rate of several meters per second; the fibers themselves can be produced up to a length of several meters. The end result is a very fine fiber web on the substrate. Through adjustment of the concentration of the solution, the attached fields, the temperature, via the use of additives and further parameters, such as additional electrodes, the viscosity, the processing temperature etc., the achieved diameters of the fibers can be adjusted within a wide range. Fibers down to several nanometers can be achieved; hereby, extensive fiber arrangements up to the square meter scale can be deposited on the substrate or the target surface.

Fibers from amorphous or partially-crystalline polymers, from block co-polymers, from polymer alloys can be created in this way. Thus, e.g., nanofibers were produced from natural and synthetic polymers as various as polyamides, polycarbonate or polymethylmethacrylate, from polynorbornene, from polyvinylidenfluoride, from cellulose, from polylactides. The precise setting of the control parameters for electrospinning is necessary for the respective material. Examples are the material of the electrode, the form and arrangement of the electrodes, the presence of auxiliary electrodes and controlling electrodes, the viscosity of the melt or solution of the template material, as well as their surface tension and conductivity. If these parameters are not optimally chosen, then drops rather than fibers will be deposited, the diameter lies in the micrometer scale or the diameters of the fibers fluctuate heavily. It is of importance for the characteristics of the fibers that, during electrospinning, it partially leads to an orientation of the chain molecules in the fibers, as was shown via electron deflection on a fiber with a diameter of around 50 nm. The orientations obtained are in fact of the same dimension as the fibers commercially heat-extruded.

A big advantage of electrospinning is that water can also be used as a solvent, so that water-soluble polymers, as well as water-soluble biological systems, can be spun. Examples are polyvinyl alcohol, polyvinylpyrrolidone, polyethylene oxide. Depending on arrangement and form of the electrodes, tissues are obtained, but also parallel strands.

Examples for results of the "nano-research" concerning this matter are i) DE 100 23 456 A1 (TransMIT, "Meso- and nanotubes"), wherein hollow fibers with an inner diameter of 10 nm to 50 µm and an outer wall, made of metal-containing, inorganic compounds, polymers and/or metals, are proposed, which can be produced according to a first method, so that a fiber from a first degradable material contains at feast one coating from at least one further material and, subsequently, the first material is degraded, provided that the hollow fibers obtained in this way feature an inner diameter of 10 nm to 50 µm.

As a second solution in the aforementioned specification, a method is proposed, whereby a fiber of a first non-degradable material is coated successively with a second, degradable material and at least one further material, and the second, degradable material is degraded, provided that, based on the at least one further material, a hollow fiber with an inner diameter of 10 nm to 50 µm and a core from the first material is obtained. The subject matter of this specification, according to claim 21, was also foreseen for application in the area of "controlled release".

ii) DE 100 40 897 A1 (TransMIT, "Production of polymer fibers with nanoscaled morphologies"), wherein porous fibers from polymeric materials are proposed; the fibers feature diameters of 20 to 4,000 nm and pores (for instance, for the absorption of active substances) in the form of channels which at least reach the core of the fiber and/or through the fiber.

These fibers are to be produced according to claim 7 of the above specification, so that a 5 to 20 percent by weight solution of at least one polymer in an easily vaporizable, organic solvent or mixture of solvents is spun by means of electrospinning at a field over $10^5$ V/m, wherein the resulting fiber features a diameter of 20 to 4,000 nm and pores in the form of channels which at least reach the core of the fiber and/or through the fiber. Hereby, surfaces of 100 to 700 m$^2$/g can be realized. According to a preferable embodiment of the subject matter of this specification (column 4, paragraphs [0028] and [0029]), fibers, which initially do not feature channels, can also be produced by using two polymers (one water-insoluble and one water-soluble). These, however, likewise show pores or channels, when, through exposure to water, the water-soluble polymers are dissolved within the pores/channels associated with them. For more precise production conditions, refer to this specification.

If the surface is structured, then changes occur in, e.g. the wetting behavior, the solution behavior and the degradation behavior, the adsorption behavior, and the ratio of surface to volume. The concept is to use a separation of phases initiated during electrospinning targeted for the formation of such surface structures (8-10). Here, on one hand, the use of a binary system of one polymer and one solvent is possible. With very volatile solvents, electrospinning leads to a depletion of the solvent and, with that, to a separation of phases under certain conditions, to the formation of a certain phase morphology, which then subsequently causes a corresponding structuring of the fibers. The regularity of the forming structure is noteworthy. Thus, this can be used very well for the production of unchanging, delaying carriers. The pores possess an ellipsoidal cross section, wherein these, e.g. in the direction of the fiber axis, are around 300 nm long and, perpendicular to that, 50 nm to 150 nm wide. The second way (see above DE 100 40 897 A1) foresees the use of ternary systems polymer1/polymer2/solvent. During the formation of the fibers, a segregation of both polymers occurs if they are incompatible. Fibers are produced with a binodal (dispersoid phase/matrix phase) or also co-continuous spinodal structure. Such composite fibers are already interesting in themselves. If one of the two components is selectively removed, then fibers with a specific surface structure result.

Unsolved up to now, however, was, in particular, the aim of how such nanoscaled fibers (thickness up to 50 µm) could be produced as carriers in the desired "large surface scale" and homogeneity concerning agricultural crop land without being stocked with plants, or how these carriers could be applied in the desired "targetedness" to plants or even to plant seeds, whereby the application of active substance per target surface (crop land surface, plant surfaces or seed surfaces) should be minimized.

AIM

Thus, the aim of the invention at hand was,
a) to provide for suitable carriers of agricultural active substances, which makes an improvement of the adjustability of the release possible
b) a method, with which the carriers, loaded or unloaded with active substance, can be released more cost-effectively in an extensive and very targeted manner with high homogeneity as well as low use of active substance per target surface, and
c) to provide for a device, with which the carrier, loaded or unloaded with active substance, can be released, according to the method based on the present invention and its further advantages, directly.

SOLUTION

Surprisingly, it was found that, with nanoscaled and/or nanostructured polymer fibers, considerably improved adjustability of the release of agricultural active substances can be achieved.

Even as surprisingly, it was found that, with a modified electrospinning method using the farmland or one or/and several plants or/and plant seeds as counter electrodes,—in the case of pure farmland—a very homogenous, extensive delivery of carriers (loaded or unloaded with active substances) can be realized with very high precision and a low use of active substance per target surface with simultaneous commercially more advantageous conditions.

In trial experiments to be considered as a further sub-invention, there was, likewise surprisingly, success in being able to "cocoon" other similar, aqueous biological systems, such as e.g. the extremities (hands, feet, arms, legs) or also other central body parts from humans or animals, in a relatively targeted manner. This is explained by the good inducibility of an electric polarization of the water in these biological systems. Overall, it was also found that, generally, dielectric substances or ferroelectric crystals are excellently suited as target surfaces for the electrospinning of polymeric solutions or/and melt.

With this sub-invention it is also possible to design the method of the coating of dielectric substances or the "cocooning" of plants to be dependant upon the moisture content of the target surfaces, i.e. without the use of additional sensors.

For this reason, a corresponding device according to the present invention features the advantage that, e.g., in the relative movement of that device over farmland with series of plants in regular distances, a spinning method is only started at those plants, which, due to sufficient moisture content, form a sufficiently strong antipole to the electric potential applied to the nozzle of the electrospinning apparatus.

In farmland without plants, the process of automatic spinning could also be carried out only on those farmland areas which feature a sufficiently high moisture concentration.

The method according to a sub-part of the present invention is thus as given below:
method for the covering of target surfaces in the form of dielectric substances or ferroelectric crystals, preferably of bodies containing water with nanoscaled fibers, wherein the target surfaces are exposed to an electric potential and thus an electric field and emanating from a nozzle, which is situated on a higher electric potential than the target surface, a solution or melt containing one polymer is deposited onto the target surface.

At the core of this sub-invention and thus this method according to the present invention is the conclusion that the distribution of the charge, formed by polarization, on the target surface or surfaces in the form of dielectric substances or ferroelectric crystals forms an antipole effective for the deposition of the polymer, together with the nozzle.

With respect to the aims mentioned further above, it must be stated, that the tasks a), b) and c) above are achieved by the subject matters of the claims 1), 4) and 14).

In Order to Solve Task a)

(The Provision of Carriers for Agricultural Active Substances)

nanoscaled polymer fibers (up to a width of 50 μm) are suggested, which were created during the known process of electrospinning.

Particularly recommended are nanoscaled polymer fibers with a diameter i) from 10 nm to 50 μm, as known from DE 100 234 56 A1 (TransMIT, "Meso- and nanotubes"), and ii) from 10 to 4,000 nm, as known from DE 100 40 897 A1 (TransMIT, "Production of polymer fibers with nanoscaled morphologies").

Concerning the coating of the meso- and nanotubes from DE 100 234 56 A1 refer to page 3 and 4 of this specification. With the methods named there or other methods for the functionalization of the tubes, as mentioned in the text, other such active substances as agrochemicals or the active substances named here or also medicinally, can be fixed in the hollow fibers. Finally, the outer wall of the fibers named there can also be composed of a biologically degradable coating, i.e. degradable under such conditions that can be found in agriculture. Examples of water-soluble materials are polyvinyl alcohol, polyvinylpyrrolidone, polyethylene oxide.

Those polymer fibers with nanoscaled morphologies, according to DE 100 40 897 A1, can, as represented on page 4, also be produced with water-soluble polymer components (see page 4 for examples). These are mixable beforehand with the agricultural active substances represented here. Finally, in this way, nanoscaled morphologies can be produced, from which the desired agricultural or also medicinal active substances are released in a delayed manner.

The mentioned nanoscaled fibers can be applied onto fields by the known methods (see above 1) to 3)), i.e. by spraying, misting, sprinkling, etc.

In the technical state of the art, the electrospinning technology is known (DE 100 23 456 "Meso- and nanotubes" refers, concerning the basics of this technology, to EP 0 005 035, EP 0 095 940 and U.S. Pat. No. 5,024,789 or WO 91/01695, for example.). The general advantage of the electrospinning method is that with this method—in comparison with the state of the art, such as other spinning methods, for example the extrusion spinning process—noticeably narrower fibres are producible and the fibres extracted in this way feature a noticeably higher surface to volume ratio.

In Order to Solve Task b)

(The Provision of a Process for the Delivery of Such Carriers)

it was decisive that, surprisingly, the known process of electrospinning is also feasible outside of laboratory conditions and mobile as well, with the necessary delivery speed, and a properly target-oriented "cocooning" of single plants or seeds (in the opened furrow and before covering with soil, or also before transfer to a field) is possible. Even with relative movement of plants/seeds or farmland in relation to the electrospinning apparatus, more than 10,000 sqm of a "nanoweb" can be delivered per day.

In this, the farmland or/and plants or/and seeds are used as a counter electrode. If necessary; additional counter electrodes are to be foreseen in the surrounding area of the plants or seeds, in order to improve the targeting of the spinning process.

The method foresees for integration of the active substances in the polymer nanofibers through blending or mixing of the polymer (or the polymer mixture) and its solvent (or solvent mixture) or its melt (or melt mixture) with the desired agricultural active substances before the process of the actual spinning.

The release of the active substances can be controlled, e.g., via diffusion and dimensions of the fibers, degradation of the fibers, dissolution of the fibers or permeation out of the fibers.

A further advantage of the method is that the process of integration of the active substances in the carriers and the delivery of the carriers/of the active substance system in nature can occur on-site (no separate packaging and storage of the carriers and active substances, etc.) and in one step.

The addition of a further biologically degradable coating, for example for the purpose of even more precise control of the diffusion or the permeation of the active substances or for the protection of the fibers, e.g. from UV rays (in delivery/spreading of the fibers to plants), can occur, for example, by the method of chemical vapor deposition, which then occurs after the exit of the fiber from the spinning nozzle or through other deposition methods not affecting the electric field.

Furthermore, a further coating can occur through a further electrospinning process, wherein the fiber emanating from the first nozzle features such a potential that polymers with the desired coating materials emanating from a second nozzle are deposited on the first fiber.

A further method known as co-electrospinning (see "Compound Core-Shell Polymer Nanofibers by Co-Electrospinning", Zaicheng Sun, Eyal Zussman, Alexander L. Yarin, Joachim H. Wendorff, Andreas Greiner; *Adv. Mat.* 15(22), pp. 1929-1932 (2003)) foresees a core- and a coating-fiber, which are basically produced simultaneously through electrospinning. For that purpose, as illustrated/depicted in the aforementioned publication under FIG. 1, the same electric potential is applied to two syringe-like containers arranged coaxially to one another and in one another, which feature separated chambers for the intake of two identical or different polymers (or polymer mixtures, in solution or/and in melted form). However, a metallic plate in the form of a copper plate was used as a counter electrode with another electric potential. With the method described there, even otherwise non-electrically spinnable polymers or substances (or mixtures thereof), such as poly(dodecylthiophenes) (PDT) in chloroform solution or even metal salt solutions such as $Pd(OAc)_2$ in tetrahydrofuran solution, were able to be electrically spun as an inner core-fiber with electrically spinnable polymers as a coating-fiber (in the first case with poly(ethylene oxide) in chloroform solution and in the second case with poly(l-lactide) in chloroform solution).

This method is thus particularly suitable as a method for the coating of polymers, which are not or very poorly electrically spinnable, as well.

Particularly suitable as a protective additive against UV radiation is, e.g. a coating made of $ZnO_xS_{(1-x)}$, preferably in crystalline form, particularly preferable in crystalline form according to the Wurtzit type, wherein this coating can also be realized on-site (thus in-situ, see above). For production, the substrate, in this case the nanoscaled fibers, is coated with the novel coat with one of the known thin-film deposition methods, e.g. with the sputter technique, the chemical vapor deposition from gas phases (CVD, MOCVD), through vaporization, through pyrolysis. Surprisingly, it was found that the mixed system ZnOS can be completely mixably synthesized as a crystalline thin-film and, in the production, the parts of O and S can be adjusted in the entire area (from x=0 to x=1), wherein the optical functional film resulting thereof features a sharp absorption edge with very high transmission at higher wave lengths and very low transmission at lower wave lengths—in comparison to the absorption edge.

For delaying the release of active substances, here of agricultural active substances as well, the permeation of the active substances (if necessary, in solution with other polymers) through polymer films is exceptionally suitable.

Suitable polymer films for delaying the release through permeation (and/or diffusion) comprise or contain:
polymers, such as poly-(p-xylylenes), polyvinylidenhalogenides, polyester, polyether, polyolefines, polycarbonates, polyurethanes, natural polymers, polycarboxylic acids, polysulfonic acids, sulfated polysaccharides, polylactides, polyglycosides, polyamides, polyvinyl alcohols, poly-α-methylstyrenes, polymethacrylates, polyacrylnitriles, poly-(p-xylylenes), polyacrylamides, polyimides, polyphenylenes, polysilanes, polysiloxanes, polybenzimidazoles, polybenzothiazoles, polyoxazoles, polysulphinides, polyesteramides, polyarylene-vinylenes, polyetherketones, polyurethanes, polysulfones, ormoceres, polyacrylates, silicones, fully aromatic co-polyesters, poly-N-vinylpyrrolidones, polyhydroxyethylmethacrylates, polymethylmethacrylates, polyethylene terephthalates, polymethacrylonitriles, polyvinyl acetates, neoprene, buna N, polybutadienes, polytetrafluorethylene, modified or unmodified celluloses, α-olefines, vinylsulfonic acids, maleic acids, alginates or collagens.

The monomers, which form the basis of the polymers, can carry one or several functional groups respectively, whereby it can concern a single or different types of substituents. It concerns the following functional groups:
H, linear or branched alkyl, alkenyl, alkinyl, cycloalkyl, cycloalkenyl, cycloalkinyl, phenyl, phenylalkyl, phenylalkenyl, phenylalkinyl, phenylcycloalkyl, phenylcycloalkenyl, phenylcycloalkinyl, cycloalkyl-alkyl, cycloalkyl-alkenyl, cycloalkyl-alkinyl, heterocyclic compounds, heterocycloalkyl, heterocyclo-alkenyl, heterocyclo-alkinyl, linear or branched alkyl sulfonate, alkenyl sulfonate, alkinyl sulfonate, linear or branched alkyl benzene sulfonate, alkenyl benzene sulfonate, alkinyl benzene sulfonate, aminosulfonyl-alkyl, aminosulfonyl-alkenyl, aminosulfonyl-alkinyl, aminosulfonyl-cycloalkyl, aminosulfonyl-cycloalkenyl, aminosulfonyl-cycloalkinyl, linear or branched alkylsulfonamide, alkenyl-sulfonamide, alkinyl-sulfonamide, cycloalkyl-sulfonamide, cycloalkenyl-sulfonamide, cycloalkinyl-sulfonamide, phenyl-sulfonamide, heterocyclo-sulfonic acid, heterocyclo-sulfonamide, heterocyclo-alkyl-sulfonic acid, heterocycloalkyl-sulfonamide, heterocyclo-alkenyl-sulfonic acid, amide- or ester-like bound linear and/or branched chain aliphatic sulfonic, carboxylic and/or phosphonic acid, styrenesulfonic acid, anetol-sulfonic acid, styrene phosphonic acid, heterocyclo-alkenyl sulfonamide, heterocyclo-alkinyl-sulfonic acid, heterocyclo-alkinyl-sulfonamide, aryl-sulfonic acid, aryl-sulfonamide, aryl-alkyl-sulfonic acid, aryl-alkyl-sulfonamide, aryl-alkenyl-sulfonic acid, aryl-alkenyl-sulfonamide, aryl-alkinyl-sulfonic acid, aryl-alkinyl-sulfonamide, alkyl-, alkenyl, alkinyl-, aryl-, heteroalkyl-, heteroaryl- carboxylic acids, esters thereof, carboxylic acid amides thereof, amino acids, orthologous phosphonic acid derivatives of all sulfonic acids listed, hydroxy-alkyl-, hydroxyalkenyl-, hydroxy-alkinyl-, hydroxy-cycloalkyl-, hydroxyalkyl-cycloalkyl-, hydroxy-cycloalkyl-alkyl-, hydroxyphenyl-, hydroxy-alkyl-phenyl-, hydroxy-phenyl-alkylgroups, as well as the orthologous amino- and thiocompounds, polyethoxy-alkyl, polyethoxy-alkenyl, polyethoxy-alkinyl, polyethoxy-cycloalkyl, polyethoxy-cycloalkenyl, polyethoxy-cycloalkinyl, polyethoxy-aryl, polyethoxy-alkyl-aryl, polyethoxy-heterocycloalkyl, polyethoxy-heterocycloaryl, alkenal, alkanal, alkinal, cycloalkenal, benzyl carbaldehyde, heteroaryl-carbaldehyde, benzyl-alkyl-carbaldehyde, heteroaryl-carbaldehyde, aliphatic heteroalkyl-alkenal, hetero-alkenyl-alkenal, heteroalkinyl-alkenal, alkanon, alkenon, alkinon, cycloalkyl-alkanon, dicycloalkanon, arylalkanon, heteroaryl-alkanon, imines, halogens and halogenated derivatives of all groups listed, nitriles, isonitriles, sulfonic acid esters, phosphonic acid esters, nitro compounds, hydroxylamines, allyl compounds, adenosine-3',5'-monophosphate, adenosine-3',5'-diphosphate, adenosine-3',5'-triphosphate, guanosine-3',5'-monophosphate, guanosine-3',5'-diphosphate, guanosine-3', 5'-triphosphate, dextran sulfate cellulose, cation exchanging groups, anion exchanging groups. Preferably, therein,
 alkyl refers to a group with 1 to 20 carbon atoms
 alkenyl and alkinyl refer to a mono- or polyunsaturated group with 3 to 20 carbon atoms
 the heterocyclic groups refer to an R group with 1 to 20 carbon atoms, wherein up to 5 carbon atoms can be replaced by heteroatoms, which are selected from the group nitrogen, oxygen, sulfur, phosphorus
 aryl refers to an aromatic R group with 5 to 20 carbon atoms
 heteroaryl refers to a corresponding aromatic R group, in which up to 5 carbon atoms can be replaced by heteroatoms from the group nitrogen, oxygen, sulfur, phosphorus.

Such films have, as e.g. in the example of polylactides shown further below, already been produced through electrospinning, in particular in the form of hollow fibers, i.e. the wall of the hollow fiber formed the polymer film functioning as the permeation barrier. Such films are, however, also able to be deposited as an electrospun coating layer on an electrospun core-fiber.

In Order to Solve Task c)
(Device)
 an electrospinning device is recommended, which features a voltage supply source able to deliver an electrical current of between 1 and 100 kV, as well as a nozzle/tip/syringe electrically connected therewith. Preferably, the device features storage means, or/and for mixing of the used polymers, solvents and agricultural active substances. The device for the production and delivery of the loaded or unloaded carriers is preferably attached to a tractor in a mobile manner and preferably uses the same energy source as the tractor as an energy source for the generation of electrical current. Alternatively, the device also features means of converting and, if necessary, storing energy in form of electrical energy.

In an advantageous practical embodiment, the device according to the present invention features at least one counter electrode electrically and/or mechanically connected to the device, for improved control of the delivery process, which features a different electrical potential to the nozzle or tip used as the first electrode for the passage of the polymer(s).

If, e.g., two counter electrodes, each to the left and right of a plant row, are arranged beneath the device moved over the field, then, if necessary, with use of further control electrodes, delivery of the carrier targeted only on these plants can be carried out.

A further, quite particularly advantageous practical embodiment for the method and device results, when for further increased specific or more targeted delivery, i.e., for example depending on the local ground composition or the condition of any one plant or down to each individual leaf, one or several optical sensors according to DE 44 13 739 are used in order to use the infrared radiation emanating from the ground or a plant or a leaf for identifying a plant (compared to normal farmland) or to identify the local composition of a soil or plant and to return the corresponding control commands to the device. (See claim 1 for the method and claim 2 and following claims of the specification quoted above for the relevant set-up).

In a further advantageous practical embodiment it is foreseen that a second, then outer nozzle/tip/syringe is provided coaxially to a first, then inner nozzle/tip/syringe. Both of the two nozzles/tips/syringes can be connected for the supply of polymers to the melt or solution to its own or a shared storage container. In addition, storage containers for the active substances can also be foreseen.

Preferably, the device also features pressurizing means, which pressurizes one or both of the containers provided, in order to supply the nozzle(s)/tip(s)/syringe(s) with polymers and/or active substances. Hereby, the blending or mixing of the polymers with the active substances can take place in the storage container or on the flow route to the nozzle, for instance by means of a collective flow route of polymer and active substance up to the tip of the device, which is arranged in such a way that turbulences in the flow and, thus, a blending of polymers and active substances can be observed.

Both of the nozzles or tips of the device feature the same electrical potential. For the production of multilayered fibers the device can feature further nozzles or tips, which are arranged around the respectively interior nozzle.

Examples for agricultural active substances are:

Examples for fungicides are:

2-aminobutane; 2-anilino-4'-methyl-6-cyclopropyl-pyrimidine; 2',6'-dibromo-2-methyl-4'-trifluoromethoxy-4'-trifluoromethyl-1,3-thiazol-5-carboxanilide; 2,6-dichloro-N-(4-trifluoromethylbenzyl)-benzamide; (E)-2-methoxyimino-N-methyl-2-(2-phenoxyphenyl)-acetamide, 8-hydroxychinoline sulfate; methyl-(E)-2-2-[6-(2-cyanophenoxy)-pyrimidine-4-yloxy]-phenyl-3-methoxyacrylate;

methyl-(E)-methoxyimino[alpha-(o-tolyloxy)-o-tolyl]-acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulfide, captafol, captan, carbendazim, carboxin, chinomethionat (quinomethionate), chloroneb, chloropicrin, chlorothalonil, chlozolinate, cufraneb, cymoxanil, cyproconazole, cyprofuram, dichlorophen, diclobutrazol, dichlofluanid, diclomezine, dicloran, diethofencarb, difenoconazole, dimethirimol, dimethomorph, diniconazole, dinocap, diphenylamine, dipyrithione, ditalimfos, dithianon, dodine, drazoxolon, edifenphos, epoxiconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoroimide, fluquinconazole, flusilazole, flusulfamide, flutolanil, flutriafol, folpet, fosetyl-aluminum, phthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations, such as: copper hydroxide, copper naphthenate, copper oxychloride, copper sulfate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram, 8-tert.-butyl-2-(N-ethyl-N-n-propyl-amino)-methyl-1,4-dioxa-spiro-[4,5]decane, N—(R)-(1-(4-chlorphenyl)-ethyl)-2,2-dichlor-1-ethyl-3t-methyl-1r-cyclopropanecarboxylic acid amide (diastereomer mixture or isolated or single isomers), [2-methyl-1-[[[1(4-methylphenyl)-ethyl]-amino]-carbonyl]-propyl]-carbamic acid 1-methylethyl ester and 1-methyl-cyclohexyl-1-carboxylic acid-(2,3-dichlor-4-hydroxy)-anilide.

Examples of bactericides are:

bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Examples of acaricides, insecticides and nematicides are:

abamectin, acephate, acrinathrin, alanycarb, aldicarb, alphamethrin, amitraz, avermectin, AZ 60541, azadirachtin, azinphos A, azinphos M, azocyclotin, *Bacillus thuringiensis,* 4-bromo-2-(4-chlorphenyl)-1-(ethoxymethyl)-5-(trifluoromethyl)-1H-pyrrole-3-carbonitrile, bendiocarb, benfuracarb, bensultap, betacyfluthrin, bifenthrin, BPMC, brofenprox, bromophos A, bufencarb, buprofezin, butocarboxim, butylpyridaben, cadusafos, carbaryl, carbofuran, carbophenothion, carbosulfan, cartap, chlorethocarb, chlorethoxyfos, chlorfenvinphos, chlorfluazuron, chlormephos, N-[(6-chloro-3-pyridinyl)-methyl]-N'-cyano-N-methyl-ethanimidamide, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton-M, demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimfos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fluazuron, flucycloxuron, flucythrinate, flufenoxuron, flufenprox, fluvalinate, fonofos, formothion, fosthiazate, fubfenprox, furathiocarb, HCH, heptenophos, hexaflumuron, hexythiazox, imidacloprid, iprobenfos, isazophos, isofenphos, isoprocarb, isoxathione, ivermectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, nitenpyram, omethoate, oxamyl, oxydemeton M, oxydeprofos, parathion A, parathion M, permethrin, phenthoate, phorate, phosalone, phosmet, phosphamidon, phoxim, pirimicarb, pirimiphos M, pirimiphos A, profenophos, promecarb, propaphos, propoxur, prothiofos, prothoate, pymetrozine, pyraclofos, pyridaphenthione, pyresmethrin, pyrethrum, pyridaben, pyrimidifen, pyriproxifen, quinalphos, salithion, sebufos, silafluofen, sulfotep, sulprofos, tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathene, triazophos, triazuron, trichlorfon, triflumuron, trimethacarb, vamidothion, XMC, xylylcarb, zetamethrin, substituted propargylamines, as shown in DE 102 17 697, dihalogenpropene compounds, as shown in DE 101 55 385, pyrazolyl benzyl ether, as shown in DE 199 61 330, pyrazole derivatives, as shown in DE 696 27 281.

Examples of herbicides are:
anilides, such as e.g. diflufenican and propanil; aryl carboxylic acids, such as e.g. dichlorpicolinic acid, dicamba and picloram; aryloxyalkanoic acids, such as e.g. 2,4-D, 2,4-DB, 2,4-DP, fluoroxypyr, MCPA, MCPP and triclopyr; aryloxyphenoxyalkanoic acid esters, such as e.g. diclofop-methyl, fenoxaprop-ethyl, fluazifop-butyl, haloxyfop-methyl and quizalofop-ethyl; azinones, such as e.g. chloridazon and norflurazon; carbamates, such as e.g. chiorpropham, desmedipham, phenmedipham and propham; chloroacetanilides, such as e.g. alachlor, acetochlor, butachlor, metazachlor, metolachlor, pretilachlor and propachlor; dinitroanilines, such as e.g. oryzalin, pendimethalin and trifluralin; diphenyl ethers, such as e.g. acifluorfen, bifenox, fluoroglycofen, fomesafen, halosafen, lactofen and oxyfluorfen; ureas, such as e.g. chlortoluron, diuron, fluometuron, isoproturon, linuron and methabenzthiazuron; hydroxylamines, such as e.g. alloxydim, clethodim, cycloxydim, sethoxydim and tralkoxydim; imidazolinones, such as e.g. imazethapyr, imazamethabenz, imazapyr and imazaquin; nitriles, such as e.g. bromoxynil, dichlobenil and ioxynil; oxyacetamides, such as e.g. mefenacet; sulfonylureas, such as e.g. amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates, such as e.g. butylates, cycloates, diallates, EPTC, esprocarb, molinates, prosulfocarb, thiobencarb and triallates; triazines, such as e.g. atrazine, cyanazine, simazine, simetryne, terbutryne and terbutylazine; triazinones, such as e.g. hexazinone, metamitron and metribuzin; others, such as e.g. aminotriazole, benfuresate, bentazone, cinmethylin, clomazone, clopyralid, difenzoquat, dithiopyr, ethofumesate, fluorochloridone, glufosinate, glyphosate, isoxaben, pyridates, quinchlorac, quinmerac, sulphosate and tridiphane.

Chlorocholine chloride and ethephone shall be named as examples for plant growth regulators.

Common inorganic or organic fertilizers for the provision of plants with macro- and/or micronutrients are named as examples for plant nutrients. All common substances applicable in preparations of this type are considered as additives which can be contained in the agricultural active substances according to the present invention. Preferably, filler materials, greases and lubricants, softening and stabilizing agents known in synthetic technology are preferably to be considered.

Examples of filler materials are:
table salt, carbonates, such as calcium carbonate or sodium hydrogen carbonate, further aluminium oxides, silicic acids, aluminas, precipitated or colloidal silicium dioxide, as well as phosphates.

As examples of greases and lubricants shall be mentioned: magnesium stearate, stearic acid, talcum and bentonite.

All substances, which are used in their common form for this purpose in polyesteramides, are considered as softening agents.

Esters of phosphoric acids, such as dimethylphthalate and dioctylphthalate, and esters of adipinic acids, such as diisobutyl adipate, further esters of azelaic acid, malic acid, citric acid, maleic acid, ricinoleic acid, myristic acid, palmitic acid, oleic acid, sebacic acid, stearic acid, and trimellitic acid, as well as complex linear poly esters, polymer softening agents and epoxidized soybean oils.

Antioxidants and substances which protect the polymers from undesired degradation during processing are considered as stabilizing agents. All commonly applicable dyes for agricultural active substances can be contained as dyes in the active substances according to the present invention. The concentrations of the individual components can be varied within a larger scale in the agricultural active substances.

PRODUCTION EXAMPLES FOR NANOSCALED POLYMER FIBERS

Examples for the production of nanoscaled polymer fibers are known from DE 100 40 897 A1 (TransMIT, "Production of polymer fibers with nanoscaled morphologies") or DE 100 234 56 A1 (TransMIT, "Meso- and nanotubes").

METHOD EXAMPLES

One first polymer is mixed or blended with active substance or/and a second polymer of the same type and then with an active substance, in a spinning apparatus, i.e. located in the nozzle or the storage container attached to the nozzle. A first electrical potential is applied to the nozzle and if necessary to the storage container, which features a different value to the target surface(s) arranged in a spaced manner to the nozzle, whereupon a thin, fiber-shaped mold made of a mixture of the aforementioned substances is deposited on the target surface or surfaces. The at least one polymer can hereby exist in the form of a solution or a melt. In the latter case, a heating of the nozzle or/and the storage container can be foreseen. The mixture/blend of polymer and active substance can also take place within the device, at the latest, however, on the flow route to the nozzle of the device.

For the delivery of the active substances, the corresponding device is moved relatively to the farmland or the plants on the ground, wherein the method of application with seeds can be carried out as a partial step of a sowing as well, such as for example in DE 43 39 443 (Amazonen factories), preferably before covering the seeds with soil. In this case, the furrows made by the plow or/and the seeds serve as a counter electrode.

It has been shown that a plant can be nearly completely "cocooned" with this process.

For improving the degree of extensive "spinning", the method can be carried out while moving the nozzle or tip/syringe of the electrospinning device relatively to the direction of movement of the device or of target area, preferably above the plant. Alternatively, several nozzles can be foreseen next to one another in a circular form or on the left and right of one or several plant rows, which can also be operated alternatingly, so that extensive "cocooning" occurs. It has been shown in experiments that 10 and more nozzles can be used parallel to one another, whereby, then, 10 plant rows or furrows can be "spun" parallelly.

A further example for the execution of the method, i.e. the "cocooning" of plants, is shown in the following for the plants maidenhair fern and baby's tears. For proof of the durability of the fibers as carriers in the form of nanoscaled polymers, poly(lactide) was chosen here.

No active substance was integrated, as the integration is already known in the technical state of the art. Thus, numerous, soluble active substances, in particular in the solution of the polymers used, as well as medicinal active substances, such as dexamethasone etc., were already integrated by the work group of the inventors work groups.

In these experiments, a counter electrode (second electrode), which is not entirely necessary, was foreseen beneath the plants (situated in a clay pot, respectively). The first electrode consisted of a centrally perforated disc, to which, compared to the second electrode (counter electrode), a low electric potential (20.15 to 30.25 kV) was applied. The nozzle featured a metallic tip with a diameter of 0.3 mm (interior), which penetrated the central opening of the perforated disc, and was located in electric contact with the perforated disc (i.e. at the same electric potential), wherein the tip protruded downwards below the level of the perforated disc.

Due to the low viscosity of the polymer solution chosen here, a storage container in a cylindrical form with a volume of 2 ml was fixed mounted above the tip, so that the device altogether featured the form of a syringe.

At a feed of the piston of 1 cm/hr, at a flow of the polymer solution of 0.7 ml/hr, a state of equilibrium between removal of the material through electrospinning and feeding by moving the piston was thus able to be achieved.

Poly(lactide) fibers with a diameter of 1 to 2 μm were deposited on a maidenhair fern and a baby's tears from a solution by electrospinning. The conditions during spinning were

|  | maidenhair fern | baby's tears |
|---|---|---|
| concentration of the solution | 4 wt % | 4 wt % |
| solvent (boiling pt.) | Dichloromethane | Dichloromethane |
| distance between the electrodes | 38.0 cm | 21.7 cm |
| height of the plant | max. 38 cm | 9.2 cm |
| diameter of the plant | max. 40 cm | 12 cm |
| distance between syringe and plants | varied | 12.5 cm |
| tension (syringe) | 20.0 kV | 15.0 kV |
| energy (syringe) | 175 nA | n.d. |
| tension (counter electrode) | 30.0 kV | 25.0 kV |
| energy (counter electrode) | 205 nA | n.d. |

In particular in long-branched plants, such as the maidenhair fern, it has been shown that a relative movement of the plant to the nozzle (first electrode) is advantageous, in order to shorten the duration of the "spinning".

Regarding the durability of the fibers, it was determined that the fibers adhered securely to the plants even after months. The growth of the plants—in particular of the baby's tears—was not influenced by the fiber mat deposited in a planar manner.

Examples of Device

The device according to the present invention features the means included in the description of the method, whereby for operation just one energy source and one electrically connected nozzle, tip/syringe are essential for the passage of the polymer. Preferably, at least one storage container for the polymer and active substance connected to the nozzle, if necessary with means of mixing or/and means of heating, (in the case of melts, instead of solutions) is foreseen.

For the improved control of the passage of the mixture of polymer and active substance a pressure device is foreseen, which exerts pressure on the mixture in the direction of the nozzle outlet. This pressure device can be connected to the optimal control of the flow speed of the mixture with a control device, which itself is connected to a transducer, such as flow or streaming speed sensors.

In the case of melts or also with rapidly changing operating temperatures (delivery in winter/spring or summer) it is advantageous to connect the supplied heating device for pre-warming the melt or the mixture or solution with the signaller and one or more temperature sensors.

In this way, the continual delivery of nanoscaled polymer fibers which remain the same (with or without active substances) can be controlled depending on the actual values of the flow or streaming speed in the nozzle or nozzle tip or depending on the temperature or temperatures of the melt/the mixture/the solution.

Preferably the device is designed to be mobile so that it can be moved over plants or farmland. A stationary device can also be foreseen, in order to be used, for instance, in greenhouses, where for example plant boxes or similar can be moved relatively to the device.

Plant seeds can also be webbed with a stationary device of the aforementioned type, which move for example on a conveyor belt relatively to the device. In both of the above cases (greenhouse, cocooning of plant seeds) it is advantageous when the plants or the plant seeds to be cocooned are exposed in a targeted manner through a counter electrode (second electrode), for instance in form of a metal frame, to an electrical field around the plants, for instance in the plant boxes of a greenhouse, or around or above a conveyor belt with the plant seeds spread on it. For the homogenous webbing of the plants or plant seeds it can be advantageous to apply alternating voltage.

Preferably, for application on the field, the energy source receives via adapted transformers, its energy from the drive device of the device carrying tractor. For the simultaneous processing of several plant rows or field sections the device features several nozzles or hoses for the output of the carriers, which for example can be arranged in pairs one to the left and one to the right of the plant row.

In a further practical embodiment the nozzles are attached to moveable arms, which are arranged in a stretched position for operation and are able to be moved for road transport into a second position, whereby the arms in the latter position are arranged parallel and next to each other. Preferably the arm parts and distances between the nozzles feature the size and distance ratios given in DE 100 41 148 A1 (Claim 1).

For increasing the "plaiting" of the carriers (nanoscaled fibres) to be observed, in particular with plants, in a particularly preferable embodiment the device features further means of moving the nozzles relatively to the plants. These means can be active means such as electric motors or similar or passive means, such as flow blade elements which use the air stream caused by the movement of the whole device for moving the nozzles. Likewise, the connection of electrical alternating voltage is suitable in order to cause an increased plaiting of the nanoscaled fibers with the plants.

In a further practical embodiment, the device can feature means for the measurement and steering or/and control of the amount of carriers delivered (mass, volume or surface of the nanoscaled fibers or tubes), e.g. in the form of a scale or in the form of optical recognition means e.g. in connection with a flow meter (which can also be designed in the form of an inductive flow meter for the reduction of the flow resistance). Alternatively, a flow rate meter, in connection with the known nozzle diameter, can also give information about the amount of carriers delivered per time unit in the form of nanoscaled fibers or tubes. In particular, these means could be used for the calibration of the device, which should be carried out corresponding to the seasonal changes of the environmental influences, in order to adjust the correct parameters, respectively, for the desired delivery per time unit or surface before the start of delivery. Naturally, the speed of the relative movement of the device to plants or soil or plant seeds should also be considered in this. The calibration before the start of delivery thus assumes that the relative movement is carried out with the desired speed for a predefined period of time and, correspondingly, the target requirements for the mass to be delivered, the parameter pressure on the mixture, the solution or the melt, temperature(s) on/in the nozzle or the mixture, the solution or the melt, are varied in such a way, until the desired actual value agrees with the target requirements.

A further advantageous practical embodiment for the device (and also for the method) foresees that a device for the creation of a high voltage alternating current between the first electrode (nozzle of the device) and the counter electrode (or electrodes, i.e. the target surface or surfaces). Thus, the degree of "plaiting" with the target surfaces by the fibers can be increased.

This alternating current can also be created mechanically and, preferably, by one or several movable, preferably rotating nozzles in the form of hooks or bar-shaped electrodes.

In a particularly preferable practical embodiment, the device features two or more nozzles arranged coaxially to one another for the output of the polymer(s). Preferably, the output openings of all of these nozzles are located in a plane and feature the same electric potential, so that co-electrospinning is able to be carried out by means of these nozzles, so that a core- and a coating-fiber can be produced.

In a further embodiment, the device features other means for coating of the nanoscaled fibers emanating from the first nozzle (i.e. the first electrode). These means are preferably the known means for the execution of thin-film deposition methods, e.g. the means of sputter technology, the chemical vapor deposition from gas phases (CVD, MOCVD), vaporization techniques and pyrolysis.

It is immediately clear to persons skilled in the art that, in particular, the carriers known from DE 100 234 56 A1 (Trans-MIT, "Meso- and nanotubes") and DE 100 40 897 A1 (Trans-MIT, "Production of polymer fibers with nanoscaled morphologies") also feature as such a use for agriculture.

The latter exists in the natural substance "air", which allows for tilling of the same when introduced into the soil. The bonding of water in these carriers results in an agricultural "use".

It is likewise clear to persons skilled in the art that other biological systems with a similarly high percentage of water can also be covered or coated with a "nano"-web with the method introduced here. In addition, e.g. the extremities of humans or animals also count, wherein, naturally, the agricultural substance would have to be replaced by medicinal or veterinarian substances. The conditions for the "webbing" of these other biological systems (extremities or entire bodies) are comparable in all parameters, such as typical potential differences, currents, distances etc., as long as it is comparable to the moisture content of the target surfaces.

BIBLIOGRAPHY

Bibliography: A

Brooks, T. W., Doane, C. C., Osborn, D. G., Haworth, J. K. (1980). Experience in using a hollow fibre controlled release formulation in pheromone mediated suppression of *Pectinophora gossypiella* under humid tropical conditions. In: R. Baker, ed., Controlled Release of Bioactive Materials, pp. 227-236. New York: Academic Press.

Brooks, T. W., Doane, C. C., Staten, R. T. (1979). Experience with the first commercial pheromone communication disruptive for suppression of an agricultural insect pest. pp 375-388. In: Chemical Ecology: Odour Communication in Animals, ed. F. J. Ritter. Amsterdam: Elservier/North Holland Biomedical. ISBN 0-444-80103-0.

Cardarelli, N. F. 1979. The efficacy, environmental impact and mechanism of release and dispersal of pesticide materials emitted from a controlled-release dispenser. pp. 744-753 in H. Geissbühler, ed. Advances in pesticide research. Part 3. IUPAC. Oxford: Pergamon Press.

Hummel, H. E., Miller, T. A., eds (1984). Techniques in Pheromone Research. Springer, New York. ISBN 0-387-90919-2

Hummel, H. E., Metcalf, R. L. (1996). *Diabrotica barberi* and *D. virgifera virgifera* fail to Orient Towards Sticky Traps in Maize Fields Permeated with the Plant Kairomones p-methoxy-phenylethanol and p-methoxy-trans-cinnamaldehyde. Med. Fac. Landbouww. Univ. Gent 61/3b, 1011-1018.

Hummel, H. E., Hein, D. F., Metcalf, R. L. (1997). Orientation disruption of Western Corn Rootworm Beetles by Air Permeation with Host Plant Kairomone Mimics. p. 36 in: 2nd FAO WCR/TCP Meeting and 4th International IWGO Workshop, Oct. 28-30, 1997, Gödöllö, Hungary, J. Kiss, ed.

Hummel, H. E., Metcalf, R. L., Lampman, R. L., Novak, R. (1998). Chemical ecology of *Diabrotica virgifera* virgifera beetle communication: orientation disruption of both sexes by permeation of Illinois maize fields with p-Methoxy-cinnamaldehyde. IWGO Newsletter XVIII (2): 29.

Hummel, H. E.; Hein, D. F., Metcalf, R. L. (1998). Orientation disruption of Western Corn Rootworm Beetles by Air Permeation with Host Plant Kairomone Mimics. IWGO Newsletter 18 (1): 34-35.

Kydonieus, A. F., ed. 1982. Controlled release technologies. Methods, theory, and applications. Vols. 1 and 2. Boca Raton, Fla.: CRC Press.

Kydonieus, A. F. and M. Beroza, eds. 1982. Insect suppression with controlled release pheromone systems. Vols. 1 and 2. Boca Raton, Fla.: CRC Press.

Leonhardt, B. A., Beroza, M. (eds.) (1982). Insect pheromone technology: chemistry and applications. ACS Symposium Series #190. American Chemical Society, Washington D. C. ISBN 0-8412-0724-0.

Plimmer, J. R., Inscoe, M. N. (1979). Insect pheromones: Some chemical problems involved in their use and development. pp. 249-260. In: Chemical Ecology: Odour Communication in Animals, ed. F. J. Ritter. Amsterdam: Elservier/North Holland Biomedical. ISBN 0-444-80103-0.

Quisumbing, A. R., Kydonieus, A. F., Calsetta, D. R., Haus, J. B. (1976). Proc. Contr. Rel. Pest. Symp. 3. 40.

Shorey, H. H., Gerber, R. G. 1996. Use of puffers for disruption of sex pheromone communication of codling moths (*Lepidoptera*: Tortricidae) in walnut orchards. Environ. Entomol 25 (6): 1398-1400.

Weatherston, J., Golub, M. A., Brooks, T. W., Huang, Y. Y., Benn, M. H. (1981). Methodology for determining in release rates of pheromones from hollow fibres. pp. 425-443. Mitchell, E. R. (ed.): Management of insect pests with semiochemicals: Concept and practice. Plenum Press, New York, London;

Wennemann, L., H. E. Hummel. 2001. *Diabrotica* beetle orientation disruption with the plant kairomone mimic 4-methoxycinnamaldehyde in *Zea mays* L. Mitt. Dtsch. Ges. allg. angew. Ent. 13: 209-214.

Wennemann, L., H. E. Hummel, I. Ujváry, P. Sipos, A. Bándiné-Barlai, K. Szücs-Tóth. 2001. Analysis of novel formulation of the plant kairomone mimic 4-methoxycinnamaldehyde (MCA) using UV spectrometry. pp. 69-76. Proceedings: VIII *Diabrotica* subgroup meeting. XXI IWGO Conference, Padova, Italy, Oct. 27-Nov. 3, 2001.

Wennemann, L., H. E. Hummel. 2001. Use of MCA (4-methoxycinnamaldehyde) as an orientation disruption tool for adult Western Corn Rootworm *Diabrotica virgifera* virgifera LeConte. pp. 77-82. Proceedings: VIII *Diabrotica* subgroup meeting. XXI IWGO Conference, Padova, Italy, Oct. 27-Nov. 3, 2001.

Bibliography B Polymers

1) Baumgarten, P. K. J. Coll. Interf. Sci. 1971, 36, 71.
2) Larrando, J.; Manley, R. S. J. J. Pol. Sci. Phys. Ed. 1981, 19, 909.
3) Doshi, J. N.; Shrinivasan, G.; Reneker, D. H. Polym. News 1995, 20, 206.
4) Jaeger, R.; Schönherr, H.; Vansco, G. J. Macromol. 1996, 29, 7634.
5) Reneker, D. H.; Yarin, A. L.; Fong, H.; Koombhongse, S. J. Appl. Phys. 2000, 87, 9.
6) J. M. Deitzel, J. D. Kleinmeyer, J. H. Hirvonen, N. C. B. tan, Polymer 42, 8163 (2001)
7) Z. Chen, M. D. Forster, W. Zhou, H. Fong, D. H. Reneker, Macromol. 34, 6156 (2001)
8) Bognitzki, M.; Hou, H.; Ishaque, M.; Frese, T.; Hellwig, M.; Schwarte, C.; Schaper, A.; Wendorff, J. H.; Greiner, A. Adv. Mat. 2000, 12, 637.
9) Bognitzki, M.; Czado, W.; Frese, T.; Schaper, A.; Hellwig, M.; Steinhart, M.; Greiner A.; Wendorff, J. H. Polym. Eng. Sci. 2001, 41, 982.
10) Bognitzki, M.; Czado, W.; Frese, T.; Schaper, A.; Hellwig, M.; Steinhart, M.; Greiner A.; Wendorff, J. H. Adv. Mat. 2001, 13, 70.
11) J. Crank, G. S. Park, "Diffusion in Polymers", Academic Press, N.Y., 1968
12) J. Comyn Ed., Polymer Permeability, Elsevier Appl. Sci. London, 1986
13) H. B. Hopfenberg, V, Stannett in "The Physics of Glassy Polymers", R. N. Haeward Ed. Applied Science Publ. London, 1973, p. 504
14) T. V. Naylor in "Comprehensive Polymer Science, S. G. Allen Ed., Pergamon Press, N.Y., 1989
15) F. Bueche, Physical Properties of Polymers, Interscience Publ. N.Y. (1962)
16) H. G. Elias, Makromoleküle, Hüthig and Wepf, basel (1975)

The invention claimed is:

1. A method of using nanoscaled polymer fibers or nanoscaled hollow fibers with and/or without nanoscaled morphologies as carriers for agricultural or agriculturally useful active substances, wherein the nanoscaled polymer fibers or the nanoscaled hollow fibers feature a diameter of 10 nm to 6 μm and are degradable under natural environmental conditions, the method further comprising using electrospun nanoscaled polymer fibers or nanoscaled hollow fibers created by electrospinning and wherein the nanoscaled polymer fibers or the nanoscaled hollow fibers feature a surface of 100 to 700 $m^2/q$.

2. The method according to claim 1, wherein the release of the active substances out of or from the nanoscaled polymer fibers or out of or from the nanoscaled hollow fibers occurs through degradation of the nanoscaled polymer fibers or nanoscaled hollow fibers through diffusion or/and permeation.

3. The method according to claim 1, wherein the release of the active substances out of or from the nanoscaled polymer fibers or out of or from the nanoscaled hollow fibers occurs through degradation of the nanoscaled polymer fibers or nanoscaled hollow fibers through diffusion or/and permeation.

4. The method according to claim 1, wherein the nanoscaled polymer fibers or the nanoscaled hollow fibers form a nanoweb.

* * * * *